United States Patent [19]
Breen et al.

[11] Patent Number: 5,928,875
[45] Date of Patent: Jul. 27, 1999

[54] PRIMERS FOR THE DETECTION OF SPORE FORMING BACTERIA

[75] Inventors: Alexander W. Breen; Freddie L. Singleton, both of Jacksonville, Fla.

[73] Assignee: BetzDearborn Inc., Trevose, Pa.

[21] Appl. No.: 09/085,359

[22] Filed: May 27, 1998

[51] Int. Cl.[6] .............................. C12Q 1/68; C12P 19/34; C12N 15/11; C07H 21/04
[52] U.S. Cl. ........................ 435/6; 435/91.2; 536/23.1; 536/24.3; 536/24.32; 536/24.33
[58] Field of Search ..................... 435/6, 91.2; 536/23.1, 536/24.3, 24.32, 24.33

[56] References Cited

U.S. PATENT DOCUMENTS

| | | | |
|---|---|---|---|
| 4,799,545 | 1/1989 | Silver et al. | 166/246 |
| 5,049,489 | 9/1991 | Aldrich et al. | 435/6 |
| 5,137,821 | 8/1992 | Sagai et al. | 435/190 |
| 5,213,971 | 5/1993 | Kunz et al. | 435/71.2 |
| 5,430,137 | 7/1995 | Gaertner et al. | 536/24.32 |
| 5,667,993 | 9/1997 | Feitelson et al. | 435/91.2 |
| 5,674,714 | 10/1997 | Kunz et al. | 435/112 |

OTHER PUBLICATIONS

Lereclus, D. et al. Overproduction of Encapsulated Insecticidal Crystal Proteins in a *Bacillus thuringiensis* SpoOA Mutant. Biotechnology. Jan. 1995. vol. 13. No. 1. pp. 67–71.

Brown et al., "Characterization of spoOA Homologues in Diverse Bacillus and Clostridium species Identified a Probable DNA–binding Domain," *Molecular Microbiology* (1994), vol. 14, pp. 411–426.

Brill et al., "Differentiation Between Spore–Forming and Asporogenic Bacteria Using a PCR and Southern Hybridization Based Method," *Journal of Microbiological Methods*, (1997), vol. 31, pp. 29–36.

*Primary Examiner*—John L. LeGuyader
*Assistant Examiner*—Mark L. Shibuya
*Attorney, Agent, or Firm*—Richard A. Paikoff

[57] ABSTRACT

A process using polymerize chain reaction (PCR) technology is described for the detection of spore forming bacteria in paper products and paper manufacturing streams and additives. Disclosed and claimed are novel nucleotide primers which specifically amplify sporulation genes common to spore forming bacteria. These primers produce gene fragments diagnostic for the presence of spore forming bacteria.

7 Claims, No Drawings

PRIMERS FOR THE DETECTION OF SPORE FORMING BACTERIA

BACKGROUND OF THE INVENTION

The microbiological quality of paper products is critical for producers of liquid board and food packaging grade material which must meet mandated standards. Producers of other paper grades such as tissue or cupstock often adhere to these standards as well. The current standard for food packaging grade material in the United States is 250 spores/gram of paper. This is determined by the Dairyman's method, a plate count enumeration technique which requires a 48 hour incubation period. A more rapid diagnosis of a contamination problem would result in significantly less wasted product and an overall increase in mill productivity.

Paper production provides many favorable niches for the proliferation of a range of microorganisms. Among the most costly and persistent problems is control of spore forming bacteria (SFB). Unlike most bacteria, SFB can pass through the dryer sections of production to pose a contamination threat when that product is used in food packaging. Spores are resistant to all but the most toxic of biocides. These compounds pose health and safety concerns within the mill and environmental concerns outside the mill. Many *Bacillus* and *Paenbacillus* strains produce food spoilage related enzymes such as caseinase and amylase. A number of industry trends are generating more concern over the microbiological quality of paper used for food packaging. Recycled fiber which often contains starch and coating material can support microbial growth. As the fraction of recycled material going into production increases, so will the chance for contamination of the finished product. Coinciding with this increase in recycled fiber is pressure to decrease the use of biocides for control of microbial growth. Fast, reliable, simple and cost effective monitoring of product quality will increase overall production efficiency by allowing problematic populations to be controlled while at the same time permitting biocides to be applied when needed.

SUMMARY OF THE INVENTION

The present invention relates to primers which will produce characteristic DNA fragments from genes encoding a sporulation function in spore forming bacteria. Hence, these primers are useful for the detection of spore forming bacteria.

In specific embodiments, the invention pertains to the following sequence segments:

1. A forward primer designated BCF with the nucleotide sequence:

5' CAA GAA GAT GTG ACG AAA 3' (SEQ ID NO.1)

2. A reverse primer designated BCR1 with the nucleotide sequence:

5' GTT GTA TTA TAT TTC TTT GC 3' (SEQ ID NO.2)

3. A reverse primer designated BCR2 with the nucleotide sequence:

5' GTT GTG TTA AAT TTT TTG GC 3' (SEQ ID NO.3)

An important aspect of the present invention is the method by which samples are prepared for PCR amplification. Spores are extremely resistant to most methods of cell lysis, hence complicating extraction of DNA. The method of the present invention contains a spore germination (or reactivation) step. This step converts dormant spores to vegetative cells, which are then lysed by boiling. DNA released from the lysed cells provides a suitable substrate for PCR amplification. Additionally, the boiling lysis method does not require solvent extraction or alcohol precipitation of sample material. These aspects speed analysis time, reduce cost and negate any need to dispose of solvents.

The presence of spore forming bacteria is determined by the presence of a gene fragment in the size range of 346 to 365 base pairs. This fragment is visualized by agarose gel electrophoresis and comparison to DNA molecular weight standards.

DETAILED DISCLOSURE OF THE INVENTION

The present invention relates to nucleotide primers and a PCR protocol for the rapid detection of spore forming bacteria in paper products, additives and process streams. The primers were designed to amplify a gene common to all sporulating bacteria regardless of particular species (e.g., the primer set will amplify the gene from *Bacillus subtilus, B. cereus* or *C. perfringens*). No cultivation of the bacteria from the test matrix is required, thus greatly decreasing the time needed for the detection of spore forming organisms. These factors make the method amenable to field testing.

This method is based on the base complimentarity of DNA. DNA is composed of two anti-parallel strands composed of nucleotide "bases". These bases, adenine, guanine, cytosine and thymine, form specific hydrogen bonds with one another. Adenine pairs with thymine and guanine pairs with cytosine. Strands of DNA can be denatured or converted to a single strand form by alkali or heat treatment. When conditions are favorable DNA will reassociate to its double stranded conformation. The polymerase chain reaction (Mullis, U.S. Pat. Nos. 4,683,195, 4,683,202, and 4,800,159) is a commonly used method to amplify target DNA segments to detectable levels. It is currently being employed to detect many pathogenic bacteria. In this process, DNA primers of specific sequence, complementary to flanking regions of the target area, are used to prime enzymatic synthesis of DNA using a DNA polymerase. DNA polymerase requires a primer to initiate synthesis of a complementary DNA strand. Primers are short (15–22 base) stretches of nucleotides. Priming during PCR is controlled at the annealing step by temperature. Annealing conditions are experimentally determined for each primer set to allow for specificity. Following annealing, polymerization occurs as the polymerase synthesizes a complementary DNA strand. After polymerization, the PCR reaction is heated to denature all double stranded DNA. The use of a thermostable DNA polymerase, isolated from the hyperthermophile Thermus aquaticus, allows for repeated cycles of annealing, polymerization and denaturing to occur without loss of enzymatic activity. The process of PCR amplification is a routine laboratory process carried out in automated thermocyling units. The result is an exponential amplification of the targeted DNA segment. The amplified target can be detected by agarose gel electrophoresis.

The present invention focuses on the evolutionary conservation of genes mediating the process of sporulation. A subset of phylogenetically diverse bacteria are able to form spores. Most commonly found spore forming bacteria are members of the genus *Bacillus* (aerobic bacteria) and *Clostridium* (anaerobic bacteria). Sporulation is a complicated developmental process, responsive to adverse environmental conditions and under strict physiological control of the cell. Heat, starvation, and chemical perturbation include some but not all of the factors that may induce the sporulation pathway. Genes involved early in the sporulation process are highly homologous across species boundaries. Once such gene is spoOA, which has been termed a "master switch" in the sporulation process. The spoOA gene encodes a kinase responsible for signaling, via phosphorylation, other genes in the process to become active. The phosphorylation state of the spoOA kinase dictates its activity in the cell. Due to this central role in triggering sporulation, spoOA is a highly conserved gene and hence a good target gene for PCR detection.

The primers described in this invention were generated by sequence comparison of the spoOA gene from a broad spectrum of spore forming bacteria. A nucleic acid sequence alignment software program elucidated highly conserved regions of the gene. From these regions specific priming sites were chosen and appropriate primers were synthesized. A trial and error approach was used to determine the optimal sequences for primer election. The final iteration of the primer set met the following set of criteria:

i. amplification of the spoOA product from a characterized set of spore forming bacteria.
ii. target products are not generated from non-spore forming bacteria.
iii. amplification of spoOA from uncharacterized spore forming bacteria isolated from paper or paper manufacture samples.

All bacteria were tested for the ability to sporulate by standard test methods. Cultures were placed at 80° C. for ten minutes, then plated on to growth medium. Any bacteria surviving the heat treatment were characterized as capable of sporulation. Table 1 summarizes data on primer properties tested on a series of diverse bacterial cultures including Gram positive non-sporulating bacteria. It was predicted that this primer set would generate a 356 base pair (bp) product from *B. subtilus* and a 347 bp product from *B. cereus*. All bacteria which tested positive in the sporulation test produced a PCR product in the 347–356 range.

Table 1 shows the ability of the primer set to amplify the spoOA gene from a set of characterized spore forming bacteria as well as uncharacterized paper mill spore forming bacteria. Also included are a set of non-spore forming bacteria which do not have the spoOA gene and did not produce the target band.

These primers can be used to screen DNA extracts from paper, paper manufacture process water or additives to detect the presence of spore forming bacteria. This process results in greatly improved turnaround time compared to traditional plating techniques. Another aspect of the present invention was the development of a DNA extraction method for spore forming bacteria.

TABLE 1

Strains used in this study.

| Bacterial Strain | Source | PCR test |
|---|---|---|
| *Bacillus cereus* ATCC 14579 | ATCC* | + |
| *B. subtilus* ATCC 6051 | ATCC | + |
| *B. subtilus* ATCC 23059 | ATCC | + |
| *B. megaterium* ATCC 14581 | ATCC | + |
| *B. stearothermophilus* ATCC 10149 | ATCC | + |
| *B. lichenformis* ATCC 12759 | ATCC | + |
| *B. sphaericus* ATCC 4525 | ATCC | + |
| *Clostridium perfringens* | DNA only (Sigma Chemical Co.) | + |
| *Staphylococcu aureus* ATCC 25923** | Difco Laboratories | – |
| *Staphylococcus epidermis* ATCC 12228** | Difco Laboratories | – |
| *Streptococcus pyogenes* ATCC 19615** | Difco Laboratories | – |
| *Pseudomonas aeruginosa* ATCC 27853** | Difco Laboratories | – |
| *Klebsiella pneumoniae* ATCC 13883** | Difco Laboratories | – |

*American Type Culture Collection
**non-spore forming organism

The following protocol resulted in successful detection of spore forming bacteria in paper and paper manufacturing matrices. A sample e.g. paper (blended in water), starch, or protein can be assayed for contamination by spore forming bacteria.

i. An equal volume of tryptic soy medium is added to the sample and it is placed at 37° C. for 45 minutes. (One ml of sample is sufficient for assaying liquid materials). This activates spores to a vegetative form from which DNA can be extracted.
ii. The sample is boiled for 10 minutes to lyse cells and liberate DNA.
iii. A sub-sample, usually 5 microliters, is used for PCR amplification.
iv. The sub-sample is combined with 20 microliters of water, a PCR bead (as described in U.S. Pat. No. 5,593,824, herein incorporated by reference), and 2 microliters of the primer mix containing the forward and two reverse primers described above.
v. The thermocycling program is as follows:
5 minutes at 94° C.
30 seconds at 94° C., 30 seconds at 54° C., 30 seconds at 72° C. - repeat 30 times
3 minutes at 72° C.
vi. Combine PCR reaction with electrophoresis loading dye and run on 2% agarose gel.
vii. Stain gel to visualize target product.

Some samples may contain clay or a preservative added which can interfere with PCR amplification. In many cases, 10 fold or 100 fold dilution of sample material in tryptic soy medium will overcome inhibition. Positive and negative controls should accompany any samples tested and a molecular weight standard should be applied to the agarose gel.

The following are examples which illustrate the procedure for practicing the invention. These examples should not be construed as limiting.

EXAMPLE 1

Processing of samples from paper mill sites

Samples of paper are added to sterile water to form a 1% weight by volume solution. The solution is mixed to form a homogenous suspension. The suspension is combined with an equal volume of tryptic soy medium and incubated at 37° C. for 45 minutes. Other mill samples such as whitewater, head box, broke, additive storage tanks or coated calendar, are incubated in an equal volume of tryptic soy medium as described.

EXAMPLE 2

Boiling lysis and PCR Amplification

Following conversion of spores to vegetative cells, the cells are boiled for 10 minutes. Care should be taken to ensure that tubes do open during boiling. A 5 microliter sample is then added to a commercial premade PCR mix. The mix provides reagents needed for PCR reactions. When brought to a final volume of 25 microliters each PCR reaction should contain 1.5 units of Taq DNA polymerase, 10 mM Tris-HCl (pH 9.0 at room temperature), 50 mM KCl, 1.5 mM $MgCl_2$, 200 uM of each nucleotide. Sterile water and the BC (*Bacillus cereus*) primer set are added to the PCR reaction. Primers are added to a concentration of 0.5 uM. The PCR tubes are placed in a thermocycler using the program specified above.

EXAMPLE 3
Detection of PCR products

The presence of spore forming bacteria is detected by the generation of PCR products in the molecular weight range of approximately 347 to 356 base pairs. Appearance of a product derived from a particular sample indicates the presence of spore forming bacteria. Non-spore forming bacteria were found not to produce a product.

Table 1 below demonstrates PCR spore detection limits in three different paper samples.

TABLE 1

| Sample Paper | Spres/0.5 g Paper | spoOA PCR Product |
|---|---|---|
| No paper[1] | 171 ± 6.0 | + |
| No paper[1] | 22 ± 1.0 | |
| A | 114.5 ± 1.5 | + |
| A | 1.5 ± 0.5 | |
| B | 59 ± 6.0 | + |
| B | 7 ± 7.0 | |
| C | 149 ± 1.0 | + |
| C | 19.5 ± 18.5 | |

[1]broth culture of *B. cereus* spores, no paper present

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

We claim:

1. A method for the systematic identification of a sporulation gene in spore forming bacteria, wherein said method comprises:

a) amplifying a portion of said gene from total cellular DNA of said spore forming bacteria by using a primer pair selected from the group consisting of SEQ ID NO. 1, SEQ ID NO. 2 and SEQ ID NO. 3; and b) detecting the presence of said amplification product.

2. The method as recited in claim 1 wherein said spore forming bacteria are aerobic.

3. The method as recited in claim 2 wherein said aerobic spore forming bacteria are selected from the group consisting of *Bacillus cereus, Bacillus subtilus, Bacillus megaterium, Bacillus stearothermophilus, Bacillus lichenformis* and *Bacillus sphaericus*.

4. The method as recited in claim 1 wherein said spore forming bacteria are anaerobic.

5. The method as recited in claim 4 wherein said anaerobic spore forming bacteria is a *Clostridium perfringens* strain.

6. The method as recited in claim 1 wherein said spore forming bacteria are gram positive.

7. The method as recited in claim 1 wherein said amplification results in the generation of a 346–365 nucleotide-long polynucleotide.

* * * * *

```
                        SEQUENCE LISTING (1) GENERAL INFORMATION:

(iii) NUMBER OF SEQUENCES:  3

(2) INFORMATION FOR SEQ ID NO: 1:

(i) SEQUENCE CHARACTERISTICS:
          (A) LENGTH:  18 base pairs
          (B) TYPE:  Nucleic acid
          (C) STRANDEDNESS:  Single
          (D) TOPOLOGY:  Linear (ii) MOLECULE TYPE:  DNA (iii) HYPOTHETICAL:  No (iv) ANTI-SENSE:  No (vi) ORIGINAL SOURCE:
          (A) ORGANISM:Bacillus cereus
          (C) INDIVIDUAL ISOLATE:  American Type Culture
               Collection 14579
          (G) CELL TYPE:  Unicellular organism (vii) IMMEDIATE SOURCE:  Same as original source (x) PUBLICATION INFORMATION:  None (xi) SEQUENCE DESCRIPTION:  SEQ ID NO:1:

CAA GAA GAT GTG ACG AAA                                            18

(2) INFORMATION FOR SEQ ID NO:2:

(i) SEQUENCE CHARACTERISTICS:
          (A) LENGTH:  20 base pairs
          (B) TYPE:  Nucleic acid
          (C) STRANDEDNESS:  Single
          (D) TOPOLOGY:  Linear (ii) MOLECULE TYPE:  DNA (iii) HYPOTHETICAL:  No (iv) ANTI-SENSE:  No (vi) ORIGINAL SOURCE:
```

-continued

```
            (A) ORGANISM:  Bacillus cereus
            (C) INDIVIDUAL ISOLATE:  American Type Culture Collection
            14579
            (G) CELL TYPE:  Unicellular organism (vii) IMMEDIATE SOURCE:  Same as original source (x) PUBLICATION INFORMATION:  None (xi) SEQUENCE DESCRIPTION:  SEQ ID NO:2:

GTT GTA TTA TAT TTC TTT GC                                              20

(2) INFORMATION FOR SEQ ID NO:3:

(i) SEQUENCE CHARACTERISTICS:
            (A) LENGTH:  20 base pairs
            (B) TYPE:  Nucleic acid
            (C) STRANDEDNESS:  Single
            (D) TOPOLOGY:  Linear (ii) MOLECULE TYPE:  DNA (iii) HYPOTHETICAL:  No (iv) ANTI-SENSE:  No (vi) ORIGINAL SOURCE:
            (A) ORGANISM:  Bacillus cereus
            (C) INDIVIDUAL ISOLATE:  American Type Culture Collection
            14579
            (G) CELL TYPE:  Unicellular organism (vii) IMMEDIATE SOURCE:  Same as original source (x) PUBLICATION INFORMATION:  None (xi) SEQUENCE DESCRIPTION:  SEQ ID NO:3:

GTT GTG TTA AAT TTT TTG GC                                              20
```